United States Patent [19]

Fernholz et al.

[11]  4,133,962
[45]  Jan. 9, 1979

[54] PROCESS FOR THE PREPARATION OF CARBOXYLIC ACID ALKENYL ESTERS

[75] Inventors: Hans Fernholz, Kelkheim; Hans-Joachim Schmidt, Königstein, Taunus; Friedrich Wunder, Flörsheim, Main; Günter Roscher, Kelkheim, all of Fed. Rep. of Germany

[73] Assignee: Hoechst Aktiengesellschaft, Frankfurt am Main, Fed. Rep. of Germany

[21] Appl. No.: 770,837

[22] Filed: Feb. 22, 1977

Related U.S. Application Data

[63] Continuation-in-part of Ser. No. 657,637, Feb. 12, 1976, abandoned.

[30] Foreign Application Priority Data

Aug. 26, 1976 [DE]  Fed. Rep. of Germany ....... 2506141

[51] Int. Cl.² ............................................. C07C 67/05

[52] U.S. Cl. .................................................. 560/245
[58] Field of Search ..................... 260/497 A; 560/245

[56] References Cited

U.S. PATENT DOCUMENTS 3,670,014  6/1972  Fernholz et al. ................ 260/497 A Primary Examiner—Howard T. Mars
Assistant Examiner—Michael Shippen
Attorney, Agent, or Firm—Curtis, Morris & Safford

[57] ABSTRACT

Process for the preparation of alkenyl esters of carboxylic acids in the gaseous phase from carboxylic acids, olefins and oxygen or oxygen containing gases in the presence of palladium carboxylate catalysts; the carboxylic acid concentration in the feed gas being lower in the starting period of the process than the intended final concentration, and subsequently being increased either continuously or stepwise until the final concentration is attained.

2 Claims, No Drawings

PROCESS FOR THE PREPARATION OF CARBOXYLIC ACID ALKENYL ESTERS

This is a continuation-in-part application to our copending application Ser. No. 657,637 filed Feb. 12, 1976, and now abandoned.

The present invention provides a process for the preparation of carboxylic acid alkenyl esters.

It is known that carboxylic acid alkenyl esters can be prepared in the gaseous phase by reaction of a carboxylic acid with an olefin and with oxygen or oxygen containing gases at elevated temperature and optionally elevated pressure in the presence of a carrier catalyst containing palladium carboxylate. Suitable starting materials are generally carboxylic acids vaporizable under the reaction conditions and containing no more than 10 carbon atoms in the molecule, especially the unsubstituted aliphatic monocarboxylic acids having from 2 to 5 carbon atoms in the molecule. Suitable olefins are those having from 2 to 12, especially 2 to 4, carbon atoms in the molecule. Above all, the processes for the manufacture of vinyl acetate or allyl acetate by acetoxylation of ethylene or propylene are of considerable economic importance. Such processes are described for example in German Patent Specifications Nos. 1,296,138 and 1,768,984.

The present invention provides a process for the preparation of alkenyl esters of carboxylic acids in the gaseous phase by reaction of a carboxylic acid with an olefin and oxygen or oxygen containing gases at elevated temperature and optionally elevated pressure in the presence of a carrier catalyst containing palladium carboxylate and optionally activators, which comprises continuously or stepwise increasing the carboxylic acid concentration in the feed gas in the starting period of the process at a temperature of from 100° to 250° C. until the final concentration is attained; the ratio of initial concentration to final concentration of carboxylic acid being 0.1 to 0.8, and the final concentration being attained after a period of from 1 to 60 hours, preferably from 1 to 40 hours.

The process is based on the surprising observation that in the starting period of the reaction the carboxylic acid content of the feed gas is of decisive importance for performance, activity and life of the palladium carboxylate carrier catalyst. It is especially required that the initial concentration of the carboxylic acid be lower than the final concentration. By initial concentration, there is to be understood hereinafter the concentration of carboxylic acid in the feed gas adjusted at the beginning of the carboxylic acid addition. By final concentration, there is to be understood the carboxylic acid concentration in the feed gas adjusted for continuous operation. An initial concentration of carboxylic acid equal to the final concentration may result in performance disparities or a decrease of the life of the catalyst. This is valid above all when highly active catalysts having a space/time yield of more than 300 g/l . h (= g of product per liter of catalyst and hour) are used. For example, it has been observed that, when the final concentration of acetic acid in an amount of 18% by volume of acetic acid vapor in the feed gas was adjusted from the start, a palladium acetate carrier catalyst attains a maximum space/time yield of 560 g of vinyl acetate/l . h after 40 hours, which decreases to 250 g/l . h within 300 hours. In contrast to this, the same catalyst under the same reaction conditions, but starting with a lower acetic acid initial concentration and slowly increasing it to the final value of 18% by volume in the feed gas, has a practically constant space/time yield of 871 g/l . h.

Similar results have been obtained also in the oxacylation of other olefins such as propylene or isobutylene with different carboxylic acids such as propionic or butyric acid, so that the process of the invention is of general importance with respect of the starting materials.

The surprising dependence on the initial concentration of carboxylic acid in oxacylation processes is inherent in all catalysts containing palladium in the form of a carboxylate on a carrier, optionally together with activating or cocatalyzing additives. Suitable palladium carboxylates are the palladium salts of unsubstituted aliphatic monocarboxylic acids having up to 10 carbon atoms in the molecule. In many cases it is advantageous to use the palladium salt of the carboxylic acid the alkenyl ester of which is to be prepared. Preferably, salts of unsubstituted aliphatic monocarboxylic acids having from 2 to 5 carbon atoms in the molecule are used, that is, the salts of acetic, propionic, n- and isobutyric acid or of the various valeric acids. Palladium acetate is preferred above all, since this palladium carboxylate is available as commercial product, and it may be used for the reaction of acetic acid and for that of higher carboxylic acids as well.

Suitable carrier materials for the catalyst are for example carbon, aluminum oxide, silicates, spinels, aluminosilicates, silicium carbide, zirconium oxide, silica gel, silicic acid or the mixtures thereof. Especially advantageous is the use of silicic acid having a specific surface of from 40 to 300 m$^2$/g and a mean pore diameter of from 50 to 2000 Å.

Activating or cocatalyzing additives for the oxacylation of olefins according to this invention are for example alkali metal carboxylates or alkaline earth metal carboxylates such as potassium acetate, sodium acetate, lithium acetate, sodium propionate, calcium isobutyrate, magnesium acetate; suitable are also those alkali metal or alkaline earth metal compounds which are converted to carboxylates under the reaction conditions, for example hydroxides, oxides or carbonates. Suitable activating or cocatalyzing additives are furthermore those salts, compounds or complex compounds of cadmium, gold, bismuth, copper, manganese, iron, cobalt, cerium, vanadium or uranium which contain no halogen or sulfur, for example carboxylates, oxides, hydroxides, carbonates, citrates, tartrates, nitrates, acetylacetonates, benzoylacetonates, acetoacetates, acetoaurates. Especially appropriate are cadmium acetate, bismuth acetate, copper acetylacetonate, barium acetoaurate, iron citrate. Mixtures of different additives may also be used.

Oxacylation is carried out by passing carboxylic acid, olefin and oxygen or oxygen containing gas over the catalyst comprising carrier, palladium carboxylate and optionally activating additives, at a temperature of from 100° to 250° C., preferably from 120° to 220° C., and under a pressure of from 1 to 25 bars, preferably from 1 to 20 bars; non-reacted components optionally being recycled. It is advantageous to chose concentration ratios which ensure that the reaction mixture is maintained outside the interval determined by the known explosion limits. Preferably, the oxygen concentration is kept low, for example, in the case where ethylene is used, below 8% by volume (relative to the acetic acid-free gas mixture). Under certain conditions, a dilution with inert gases such as nitrogen or carbon dioxide is recommended. $CO_2$ is especially suitable as diluting agent in the case of cyclic processes, since it is formed in small amounts during the reaction.

As olefins, there may be used all unsaturated aliphatic hydrocarbons of the formula $C_nH_{2n}$ which are vaporizable and gaseous under the reaction conditions, especially those having up to 12 carbon atoms in the molecule. Especially suitable are olefins having from 2 to 4 carbon atoms in the molecule, that is, ethylene, propylene, 1-butene, 2-butene and isobutylene.

Carboxylic acids suitable for the process of the invention are unsubstituted, saturated, aliphatic monocarboxylic acids having up to 10 carbon atoms in the molecule, which are vaporizable under the reaction conditions, preferably those having from 2 to 5 carbon atoms, i.e. acetic acid, propionic acid, n- and isobutyric acid, or the various valeric acids.

The starting period of the oxacylation comprises the total time which passes until the reaction conditions intended for continuous operation and the final concentrations of the reactants are definitely adjusted. The process of the invention relates to that part of this starting period which begins with the feeding of the carboxylic acid to the reactor. At this moment, the catalyst temperature should have a level which prevents condensation of the carboxylic acid on the catalyst, that is, it should be in a range of from 100° to 250° C., preferably from 120° to 220° C. This temperature may be identical to that of the continuous operation; however, within the above limits, it may be lower or higher than the latter. The pressure at the start of carboxylic acid addition may also correspond to that of the continuous operation or attain any other value within the aforementioned limits of from 1 to 25 bars, preferably from 1 to 20 bars. However, in order to prevent the condensation of the carboxylic acid on the catalyst, it is advantageous not to exceed the pressure intended for the continuous operation.

In accordance with this invention, at the start of carboxylic acid addition, there is used such an amount of carboxylic acid which corresponds to an initial concentration of carboxylic acid in the feed gas of from 10 to 80%, preferably from 40 to 70%, of the intended final concentration. Within the remaining starting period, this concentration is increased, either continuously or stepwise, in such a manner that the final concentration of carboxylic acid is attained after a time of from 1 to 60 hours, preferably from 1 to 40 hours.

At the start of carboxylic acid addition, the feed gas consists generally of the olefin used for the oxacylation, or of a mixture of olefin and inert gas. It may however be also inert gas alone to which the olefin is added only after the start of carboxylic acid addition. Suitable inert gases are for example nitrogen or carbon dioxide.

Oxygen may be added to the feed gas at the start of carboxylic acid addition, but also before or after it. Preferably, oxygen is added only from the moment on where acetic acid is obtained in the condensation vessel for the gases leaving the reactor.

During the starting period, the oxygen concentration may be deliberately chosen outside the range determined by the explosion limits; for example, when ethylene is used the oxygen concentration in the acetic acid-free gas mixture may amount to 8% by volume. However, it is advantageous to keep low the oxygen concentration at the start and to increase it to the intended final value in a manner corresponding to the increasing carboxylic acid concentration.

The process of the invention allows to obtain higher space/time yields and higher conversion rates for a longer period than hitherto possible, so that it is especially economic.

The following examples illustrate the invention; percentages being by weight unless otherwise stated. N in Nl stands for "normal", that is, at 0° C. and 760 mm Hg.

COMPARATIVE EXAMPLE 1

1000 g (about 2 l) of a silicic acid carrier having a surface of 120 m²/g and a pore volume of 0.8 ml/g are impregnated with a solution of 46.5 g of palladium acetate, 45 g of cadmium acetate, 54.5 g of potassium acetate and 3.7 g of manganese acetate in 716 ml of acetic acid, and dried at 200 mm Hg and 60° C. under a nitrogen atmosphere. The finished catalyst contains 1.9% of palladium, 1.7% of cadmium, 2.0% of potassium and 0.07% of manganese, calculated as elements.

In an oil-heated reactor tube, at 160° C. and under a pressure of 8.5 bars (reactor inlet), a gas mixture of 5320 Nl of ethylene, 1554 Nl of inert gas (nitrogen + carbon dioxide) and 4380 g of acetic acid (= 1636 Nl of acetic acid vapor) is passed per hour over 2 liters of the above catalyst. A gradually increased oxygen amount is added to this mixture in such a manner that after 3 hours an oxygen concentration of 6.3% by volume in the gas mixture is attained. Subsequently, the temperature is raised to 180° C. The space/time yield of vinyl acetate after 40 hours is 560 g/l . h, after 140 hours 310 g/l . h and after 300 hours 250 g/l . h.

EXAMPLE 1

At 160° C. and 8.5 bars, a gas mixture of 5320 Nl of ethylene, 1554 Nl of inert gas and 1460 g of acetic acid is passed for one hour over 2 l of the catalyst described in Comparative Example 1. After this hour, the acetic acid amount is increased per hour by further 1460 g until a total per hour of 4380 g is attained. The amounts of ethylene and inert gas remain unchanged during this operation. Simultaneously, as in Comparative Example 1, the oxygen concentration is increased within 3 hours to 6.3% by volume and the temperature is raised to 180° C. within the same period. After 100 hours, the space/time yield of vinyl acetate is 871 g/l . h, and it is unchanged even after 300 hours.

COMPARATIVE EXAMPLE 2

2 l of a catalyst, prepared by impregnating 1000 g of the carrier described in Comparative Example 1 with a solution of 29 g of palladium acetate, 7 g of barium acetoaurate and 47 g of potassium acetate in 754 ml of acetic acid, and subsequently dried, are introduced into the reactor tube cited in Comparative Example 1. The catalyst contains 1.25% of palladium, 0.25% of gold, 1.8% of potassium and 0.26% of barium (calculated as elements).

At 170° C. and a pressure of 8.5 bars (reactor inlet), 8.5 Nm³ per hour of the composition described in Comparative Example 1 are passed over the catalyst. A progressively increased oxygen amount is added to this gas mixture in such a manner that after 5 hours an oxygen concentration of 6.3% by volume in the feed gas is attained. Within the same time, the reactor temperature is simultaneously raised to 178° C. The vinyl acetate space/time yield, under these conditions, is 510 g per liter of catalyst and hour after 40 hours, 290 g/l . h after 140 hours and 200 g/l . h after 300 hours.

EXAMPLE 2

At 170° C. and 8.5 bars, a gas mixture of 5320 Nl/h of ethylene, 1554 Nl/h of acetic acid is passed at the start over 2 l of the catalyst described in Comparative Example 2. After 15 minutes, the acetic acid amount is increased slowly and uniformly in such a manner that after 3 hours the same amount of acetic acid as cited in Comparative Example 1 is attained. The oxygen concentration is adjusted within 5 hours to 6.3% by volume in the gas mixture, as indicated in Comparative Example 2. A vinyl acetate space/time yield of 790 g per liter of catalyst and hour is obtained, which is the same even after 800 hours.

COMPARATIVE EXAMPLE 3

2 l of a catalyst prepared by impregnating 1000 g of the carrier cited in Comparative Example 1 with a solution of 39 g of palladium acetate, 103 g of potassium acetate and 33.5 g of copper acetylacetonate are introduced into the reactor. After drying, the catalyst contains 1.6% of palladium, 3.8% of potassium and 0.7% of copper, calculated as elements.

At a pressure of 6.5 bars (reactor inlet) and a reactor temperature of 170° C. at the start, 2000 Nl of propylene, 1925 Nl of inert gases (nitrogen and carbon dioxide) and 2600 g of acetic acid (corresponding to 970 Nl of acetic acid vapor) are passed per hour over the catalyst. A progressively increased oxygen amount is added to the gas mixture in such a manner that after 6 hours the oxygen concentration in the feed gas is 7% by volume. Within the same time, the reactor temperature is raised to 185° C. After 65 hours, a space/time yield of allyl acetate of 420 g per liter of catalyst and hour is obtained, 285 g/l . h are obtained after 135 hours and 220 g/l . h after 250 hours.

EXAMPLE 3

The process is the same as in Comparative Example 3, but at the start, a gas mixture is composed of 2000 Nl/h of propylene, 1925 Nl/h of inert gases and 1100 g/h of acetic acid (= 410 Nl/h of acetic acid vapor) is passed over 2 l of the catalyst at 170° C. Within 6 hours, the amount of acetic acid is increased uniformly to 2600 g per hour. Simultaneously the oxygen concentration is slowly increased to 7% by volume within this period, and the reactor temperature is raised to 185° C. Under these conditions, which correspond to the final conditions of Comparative Example 3, a constant space/time yield of 770 to 780 g of allyl acetate per liter of catalyst and hour are obtained.

COMPARATIVE EXAMPLE 4

1000 g, that is, about 2 l, of the carrier cited in Comparative Example 1 are impregnated with a solution of 35.5 g of palladium acetate, 15 g of barium acetoaurate, 15 g of bismuth acetate and 110 g of potassium acetate in 700 ml of acetic acid, and dried. The catalyst contains 1.4% of palladium, 0.5% of gold, 0.6% of bismuth, 3.9% of potassium and 0.2% of barium, calculated as elements.

At 185° C. and a pressure of 7 bars, 2000 Nl/h of propylene and 2200 g/h of propionic acid are passed aver 2 l of the catalyst, and a gradually increased oxygen amount is added to the gas mixture in such a manner that after 5 hours an oxygen concentration of 7.5% by volume in the gas mixture is attained. The space/time yield of allyl propionate is 220 g per liter of catalyst and hour, 154 g/l . h after 170 hours and 133 g/l . h after 220 hours.

EXAMPLE 4

At 185° C. and 7 bars, a gas mixture of 2400 Nl/h of propylene and 500 g/h of propionic acid are passed at the start over 2 l of the catalyst having the composition as indicated in Comparative Example 4. Within 5 hours, the amount of propionic acid is increased stepwise by 340 g/h to 2200 g/h. Within the same period, the oxygen concentration is adjusted to 7.4% by volume. The space/time yield of allyl propionate is 380 g per liter of catalyst and hour after 120 hours, and after a further 150 hours, it is still the same.

COMPARATIVE EXAMPLE 5

At 135° C. and a pressure of 5.5 bars, a gas mixture of 1500 Nl/h of propylene and 1335 g/h of butyric acid is passed over 1 l of the catalyst indicated in Comparative Example 4, and a gradually increased oxygen amount is added in such a manner that after 20 hours an oxygen concentration of 8% by volume in the gas mixture is adjusted. The space/time yield of allyl butyrate is 165 g per liter of catalyst and hour after 30 hours, and within a further 48 hours, it drops to 105 g/l . h.

EXAMPLE 6

The process is the same as in Comparative Example 5, but operations are started with an amount of butyric acid in the gas mixture of 335 g in the first hour, which amount is increased subsequently by 50 g per hour, until 1335 g/h are attained after 20 hours. Within the same time, the oxygen concentration in the gas mixture is adjusted to 8% by volume. The space/time yield is 258 g of allyl butyrate per liter of catalyst and hour after 30 hours, and 245 g/l . h after a further 96 hours.

COMPARATIVE EXAMPLE 6

A catalyst is used which is obtained by impregnation of 960 g (corresponding to 2 l) of an active charcoal having a pore volume of 0.85 ml/g and a surface of 950 $m^2/g$ with a solution of 34 g of palladium acetate, 20.5 of barium acetoaurate, 14 g of bisumth acetate and 103 g of potassium acetate in 720 ml of acetic acid, and which is subsequently dried. The catalyst contains 1.4% of palladium, 0.7% of gold, 0.6% of bismuth, 3.8% of potassium and 0.2% of barium (calculated as elements).

At 180° C. and a pressure of 6 bars, a gas mixture of 4000 Nl/h of isobutylene, 800 Nl/h of inert gas (nitrogen and carbon dioxide) and 3200 g/h of acetic acid (= 1200 Nl/h of acetic acid) is passed over 2 l of the catalyst. A gradually increased oxygen amount is added to the gas mixture in such a manner that after 4.5 hours an oxygen concentration in the gas mixture of 6.25% by volume is attained. The space/time yield of methallyl acetate is 240 g per liter of catalyst and hour after 24 hours, and only 155 g/l . h after 120 hours.

EXAMPLE 7

The process is as described in Comparative Example 6, but operations are started with an amount of 1500 g/h of acetic acid. After 30 minutes, the acetic acid amount is gradually increased to 3200 g/h within 4 hours, so that after 4.5 hours the mixture composed of 4000 Nl of isobutylene, 1200 Nl of acetic acid vapor, 880 Nl of inert gas and 400 Nl of oxygen is passed over the catalyst, as is described in Comparative Example 6. The space/time yield of methallyl acetate is now a constant 350 g per liter of catalyst and hour.

COMPARATIVE EXAMPLE 7

(corresponding to Example 1 of U.S. Pat. No. 3,670,014)

970 grams of a silicic acid carrier were impregnated with a solution of 40 grams of bismuth nitrate in 735 milliliters of water 67 milliliters of concentrated nitric acid. The dried catalyst was placed in a vessel containing 2 liters of a 5% potassium hydroxide solution. After the solid substance had deposited, the supernatant potassium hydroxide solution was decanted and replaced by water. The catalyst was then suction filtered, dried and impregnated with a solution of 40 grams of potassium acetate and 21.5 grams of palladium acetate in 730 milliliters of acetic acid and finally dried in vacuo at 50° C. The finished mixed catalyst contained about 1.95% by weight of palladium diacetate, 6.5% by weight of potassium acetate and 1.56% by weight of bismuth in the form of acetates.

2 liters of the catalyst obtained were introduced into a reaction tube. Under a pressure of 5 bars a mixture of 650 Nl/h of nitrogen (normal liters Nl are measured under normal conditions of temperature and pressure) and 20 Nl/h of oxygen was passed over the catalyst and the catalyst was heated to 170° C. within 1 hour. After a temperature of 100° C. had been reached, acetic acid was added to the gas streams, starting with an amount of 140 g/h which was gradually increased to reach a value of 2000 g/h as 170° C. was reached. Additionally, a constant amount of 1,600 Nl/h of propylene was added after a temperature of 130° C. had been attained. After the temperature of 170° C. had been reached within 1 hour, the amount of oxygen was gradually increased from 20 Nl/h to 196 Nl/h in the course of 36 hours, the temperature and the amounts of nitrogen, propylene and acetic acid being kept constant. A space time yield of 245 grams of allyl acetate per liter of catalyst and per hour was obtained.

EXAMPLE 7

2 liters of fresh catalyst which had been prepared under the conditions specified in Comparative Example 7 were used. Under a pressure of 5 bars a mixture of 650 Nl/h of nitrogen and 20 Nl/h of oxygen as in Comparative Example 7 was passed over the catalyst and the catalyst was heated to 170° C. within one hour. After a temperature of 100° C. had been reached, acetic acid was added to the gas stream, starting with an amount of 140 g/h which was gradually increased to reach a value of 2000 g/h within two hours (rather than 1 hour as in Comparative Example 7) after heating had started. Additionally, as in Comparative Example 7, a constant amount of 1,600 Nl/h of propylene was added after a temperature of 130° C. had been attained. After the final value of 2000 g/h of acetic acid had been reached (i.e. 2 hours after heating had started) the amount of oxygen was gradually increased from 20 Nl/h to 196 Nl/h per hour in the course of 34 hours, the temperature and the amounts of nitrogen, propylene and acetic acid being kept constant. Under the thus adjusted final conditions, which are equal to the final conditions of Comparative Example 7, a space-time yield of 360 to 365 grams of allyl acetate per liter of catalyst and per hour was obtained. Comparison with Comparative Example 7 shows that the time consumed for increasing the acetic acid concentration has a very marked influence on the space-time-yield. More precisely: if the concentration is increased to the same value within two hours instead of one (calculated from the moment when heating started) the space-time yield goes up by 50%.

What is claimed is:

1. In a process for the preparation of alkenyl esters of carboxylic acids in the gaseous phase by reaction of a carboxylic acid with an olefin and oxygen or oxygen containing gases at elevated temperature and optionally elevated pressure in the presence of a carrier catalyst containing palladium carboxylate and optionally activators, the improvement comprising, continuously or stepwise increasing the carboxylic acid concentration in the feed gas in the starting period of the process at a temperature from 100° to 250° C. until the final concentration is attained; the ratio of initial concentration to final concentration of carboxylic acid being 0.1 to 0.8, and the final concentration being attained after a period of from 1 to 60 hours.

2. The process as claimed in claim 1, wherein the final concentration of carboxylic acid is attained after 1 to 40 hours.

* * * * *

UNITED STATES PATENT AND TRADEMARK OFFICE
CERTIFICATE OF CORRECTION

PATENT NO. : 4,133,962
DATED : January 9, 1979
INVENTOR(S) : Fernholz et al.

It is certified that error appears in the above-identified patent and that said Letters Patent are hereby corrected as shown below:

In the Heading, Item [30], "Aug. 26, 1976" should be --Feb. 14, 1975--.

Signed and Sealed this

Tenth Day of April 1979

[SEAL]

Attest:

RUTH C. MASON
Attesting Officer

DONALD W. BANNER
Commissioner of Patents and Trademarks